United States Patent [19]
Stevens et al.

[11] Patent Number: 5,874,098
[45] Date of Patent: Feb. 23, 1999

[54] PELLET IMPLANT SYSTEM

[75] Inventors: Thomas L. Stevens, Parkville, Mo.; Stanford R. Spurlin, Lenexa, Kans.

[73] Assignee: Ivy Laboratories, Inc., Overland Park, Kans.

[21] Appl. No.: 864,439

[22] Filed: May 28, 1997

[51] Int. Cl.$^6$ .............................. A01N 25/34; A61F 2/02
[52] U.S. Cl. ........................................... 424/408; 424/423
[58] Field of Search .................................. 424/408, 423; 514/772.3, 777

[56] References Cited

U.S. PATENT DOCUMENTS

| | | |
|---|---|---|
| 4,066,754 | 1/1978 | Chou . |
| 4,994,227 | 2/1991 | Dietz et al. . |
| 5,035,891 | 7/1991 | Runkel et al. ........................ 424/423 |
| 5,110,595 | 5/1992 | Wang . |
| 5,152,995 | 10/1992 | Runkel et al. . |
| 5,198,222 | 3/1993 | Scully et al. . |
| 5,314,882 | 5/1994 | Pantic et al. . |
| 5,522,797 | 6/1996 | Grimm . |

*Primary Examiner*—Carlos Azpuru
*Attorney, Agent, or Firm*—Litman, McMahon & Brown, L.L.C.

[57] ABSTRACT

An antibiotic and pharmaceutical pellet system and method provides localized sustained antibiotic release as part of a single therapeutic procedure in order to prevent infections at the injection site. The system includes an implanter apparatus for subcutaneously implanting pharmaceutical pellets in an animal through the bore of a hypodermic needle which is operably coupled to a pellet magazine, a pellet magazine, and a plurality of pellets sized to be implanted through the needle and positioned in the magazine for selective alignment of a pellet with the needle. The pellets include pharmaceutical dose pellets and antibiotic dose pellets which are packaged in the magazine in sequential order for delivery of the pharmaceutical dose followed by the antibiotic dose as part of a single injection. The system permits localized controlled and sustained absorption of the antibiotic pellet dose to combat infection in and around the site of the injection.

14 Claims, 1 Drawing Sheet

PELLET IMPLANT SYSTEM

BACKGROUND OF THE INVENTION

The present invention is broadly concerned with a pellet implant system which administers an antibiotic pellet subcutaneously along with a pharmaceutical pellet implant in a single combined procedure which provides controlled, sustained localized antibiotic release in order to prevent infections at the injection site. More particularly, it is concerned with an implanter having a pellet magazine containing antibiotic and pharmaceutical pellets with an associated injection needle, as well as structure permitting injection of pellets from the magazine through the needle for implantation under the skin of an animal. The magazine is loaded with antibiotic and pharmaceutical pellets for distribution in sequence singly or in multiples into the same injection site.

Implant technology, that is to say, procedures involving subcutaneous implant of pharmaceuticals and medical devices, is now well accepted and widespread in the areas of animal health and production enhancement as well as human health. Growth stimulants are commonly used to enhance the body weight of animals which are raised for slaughtering, such as cattle, swine, sheep, turkeys, chickens, and the like.

In the case of cattle, swine and sheep, approved growth stimulants are administered as solid pellets which are injected by an implanter equipped with a hypodermic needle. The needle is used to make a surface self-sealing and, non-coring implant receiving puncture beneath the skin of the ear of the animal. Small pellets of growth hormone are forced through the needle and left under the skin as the needle is removed from the ear. The ears are commonly discarded in slaughtering, such that no unabsorbed residues of such pellets will end up in food products intended for humans or domestic animals. The pharmaceutical in the pellets is normally formulated for timed release and continuous, sustained absorption of the active ingredients over an extended period of time.

Many types of pharmaceuticals such as bioactive compounds may also be implanted and include insulin, endocrine hormones for control of reproduction, vaccines, and biocides for flea and parasite control in humans, horses, and domestic animals such as dogs and cats. The compounds may be administered subcutaneously at any suitable location on the body.

Similar therapeutic procedures may be employed to implant drug delivery devices such as controlled release osmotic pumps in humans and animals as well as transponder devices in animals.

In the case of farm animals, the pellets are normally implanted while an animal is confined in a chute. An ear is grasped in one hand, and an implanter device having a large hypodermic needle is used to puncture the hide and subcutaneously inject a pellet dose into an implant receiving puncture. The implanting must be done carefully to insure that the pellets are properly placed and that no pellet remains extending from the puncture outside the hide. The procedure must be carried out quickly since the animals are not entirely cooperative and may shake their heads to free the held ear.

It is virtually impossible in such situations to provide a sterile injection site on a single animal or to prevent transfer of infective microbes from one animal to the next on the injecting needle. Further complicating the matter is that other procedures may be occurring at the same time as the implanting operation while the animal is confined, such as ear tagging, branding, veterinary inspections or procedures, or the like, which may further excite the animal and make injecting and disinfecting difficult. It is not unusual to even have manure at the injection site.

U.S. Pat. No. 5,522,797 (hereinafter "the '797 patent"), and entitled Slide Action Veterinary Implanter, which patent is hereby incorporated by reference, discloses an implanter which employs a slide action mechanism to retract an impeller, store an impeller driving force in a spring in cooperation with a latch mechanism, reset a trigger, and advance a pellet magazine, all by a single trigger actuated reciprocation of the slide mechanism. Operation of the trigger also forces the pellets from the magazine through the needle and under the skin of the animal.

Efficient implanters such as that taught in the '797 patent permit rapid sequential injection of many animals in a single session, leaving each animal with an open implant receiving puncture at the site of each injection. The injections are administered at locations such as feedlots where skin heavily contaminated with bacteria is common. Following the procedure, the implant receiving puncture is not bandaged, leaving the puncture open to contamination caused by contact with other animals, structures or the ground and by migration across the skin.

Consequently, bacteria introduced into the implant site, either during the delivery of the implant or thereafter may cause an infection at the site. Such infections may and often do result in abscesses, which may reduce the effectiveness of the implant by encapsulation of the implant pellet or by pushing the therapeutic pellet out of the original insertion implant receiving puncture, thereby preventing absorption and transport of the active ingredients. It is estimated that from about 10% to about 15% of feedlot cattle which are implanted in the United States subsequently develop abscesses.

A variety of techniques are currently employed to reduce the incidence of abscesses. Implant manufacturers recommend disinfection of the implanting tool, pellet magazines and needles, and observation of good sanitation practices during the implantation process. The implantation site may be cleaned or disinfected prior to injection to help prevent entry of resident bacteria into the implant receiving puncture and the needle, which may be employed to inject dozens of animals, may be disinfected between animals to prevent the transfer of bacteria from one animal to the next.

In addition, attempts have been made to augment the formulation of the pharmaceutical pellets themselves with boric acid, and to dust the implants prior to sale with an antibacterial compound such as oxytetracycline.

While all such measures may serve to increase sanitation and to reduce initial contamination of the implant receiving puncture, they do not administer an effective and predetermined quantity of an antibacterial agent and do not provide sustained inhibition of bacterial growth inside the implant receiving puncture itself. Controlled, sustained release of an antibacterial agent is needed to combat both microorganisms which have been introduced during the implant process and later multiply and new bacteria which may later enter through the implant receiving puncture from the surface of the hide.

Previous sustained release antibiotics for ruminants such as disclosed by Chou in U.S. Pat. No. 4,066,754 have been administered orally in bolus form. Such antibiotic preparations are systemic, rather than localized in their effects, and they must be administered orally in a separate procedure from the pellet implantation disclosed in the '797 patent.

Accordingly, there is a need for an antibiotic or bacteriostatic pellet system which delivers subcutaneously both pharmaceutical and antibiotic or bacteriostatic pellets to provide sustained localized prevention of infections at the injection site, and which does so without causing any additional implant receiving punctures.

SUMMARY OF THE INVENTION

The present invention resolves the problems previously outlined and provides a greatly improved pharmaceutical pellet system which also delivers localized, controlled and sustained release of a predetermined quantity of an antibiotic and/or bacteriostatic compound along with the pharmaceutical implant as part of a single procedure in order to provide desired pharmaceutical to the animal while simultaneously preventing infections at the injection site.

Broadly speaking, the pellet system includes an implanter apparatus for subcutaneously implanting pharmaceutical pellets in an animal through the bore of a hypodermic needle which is remotely coupled to a pellet magazine, and a plurality of pellets sized to be implanted through the needle and positioned in the magazine for selective alignment of a pellet with the needle. The pellets include at least one pharmaceutical dose first pellet and at least one antibiotic agent dose second pellet which combined pellets are packaged in the magazine in sequential order for simultaneous delivery of a pharmaceutical dose and an antibiotic agent dose as part of a single injection. Advantageously, the system permits localized, sustained absorption of the antibiotic agent dose to combat infection in and around the site of the injection.

OBJECTS AND ADVANTAGES OF THE INVENTION

The principal objects and advantages of the present invention include: providing an antibiotic pellet system and method for use in conjunction with a pharmaceutical pellet; providing such a system and method which permits localized sustained antibiotic release at an injection site in order to combat infection in and around the site of the injection; providing a pellet system which includes an implanter apparatus for subcutaneously injecting pharmaceutical pellets in an animal through the bore of a hypodermic needle which is remotely coupled to a pellet magazine and simultaneously introduces an antibiotic, bacteriostatic or anti-inflammatory pellet into the injection site; providing such a system and method which permits injection of predetermined doses of one or more pharmaceutical and an antibiotic agent in a single injection; providing such a system and method which permits subcutaneous injection of both a pharmaceutical dose and an antibiotic agent dose; providing such a system and method which permits an operator to selectively inject an antibiotic agent dose into the needle; providing such a system and method which permits serial injection of large numbers of animals in a single session; providing such a system and method which may employ a wide range of antibiotic agents for use in abscess reduction; providing such a system and method which is simple and efficient and economical to manufacture, which effectively prevents infection at the injection site and which is particularly well-adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
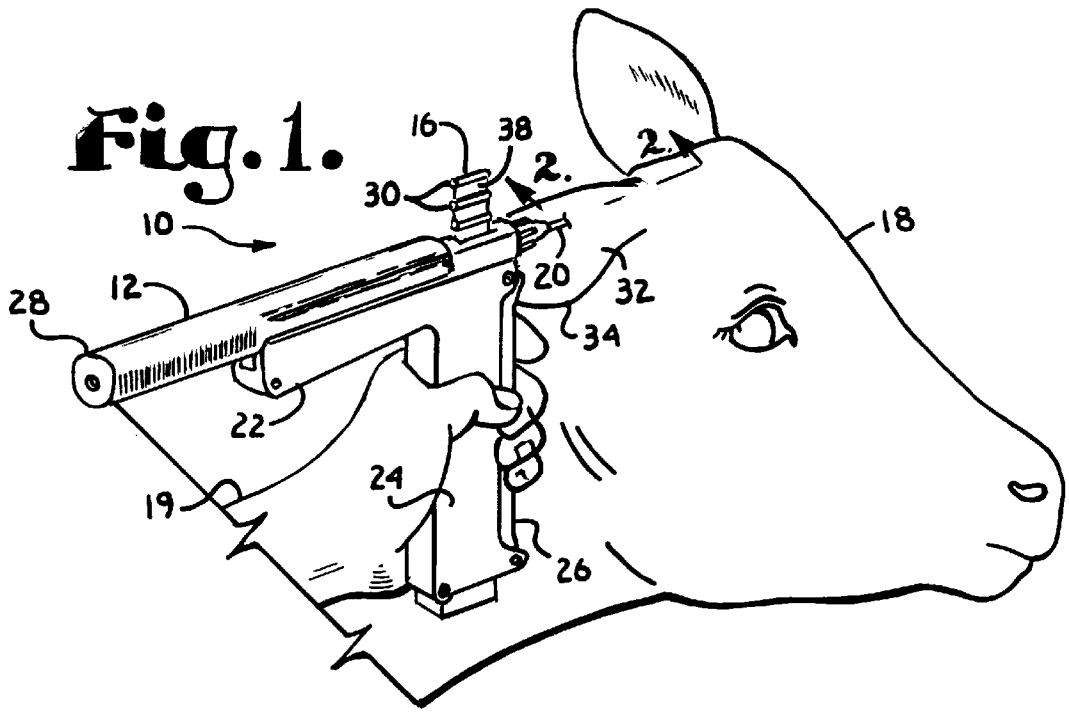
FIG. 1 is a fragmentary perspective view of a cow, an implanter apparatus in accordance with the present invention and an apparatus operator.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

In general the reference numeral 10 represents a pellet implantation system in accordance with the invention. The implantation system 10 broadly includes a slide action implanter apparatus 12 which is used to implant solid form drugs or pharmaceuticals, such as pellets 14 and antibiotic agent pellets 15 (FIG. 2) from a magazine strip 16 into an animal 18 through a hypodermic needle 20. The needle 20 is utilized by an operator 19 to create an opening 23 that produces an implant receiving puncture 21 in the animal 18.

A suitable implanter apparatus 12 is illustrated and described in detail in the '797 patent, and generally includes a housing 22 having a grip 24 with a trigger assembly 26 pivotally mounted therein. An impeller 28 is slidably mounted within the housing 22 in alignment with an interior bore 29 of the needle 20 and aligned chambers 30 of the loaded pellet magazine strip 16. The needle 20 is used to puncture through the skin or hide 32 of an animal's ear 34 at the opening 23, and the trigger 26 is squeezed toward the grip 24 of the housing 22 to initiate injection of the pellets 14 and 15 and so as to cause the impeller 28 to be urged through the magazine chamber 30 and needle bore 29, thereby forcing the pellets 14 and 15 through the bore 29 of needle 20 and into the puncture 21 in the ear 34.

Each magazine strip 16 of the implanter 12 typically contains multiple parallel aligned pellet doses stored in corresponding pellet chambers 30, which are connected by interconnecting webs 38. The chambers 30 are slightly conical in shape and are arranged in a side-by-side parallel relation. The chambers 30 may have internal frictional formations such as beads or posts (not shown) to retain the pellets 14 and 15 therein prior to insertion and which can be easily bypassed by application of pressure to the trigger 26. A plurality of strips 16 can be connected in end-to-end relation to increase the implanting capacity before the implanter 12 requires reloading. As the pellets 14 and 15 in an individual magazine strip 16 are exhausted the empty strip 16 can be detached from the remaining strips 16 located in the implanter 12 and discarded.

Each pellet chamber 30 is loaded with multiple discrete pellets 14 and in the present embodiment the single antibiotic agent pellet 15. The pellets 14 and 15 are composed of one or more active ingredients, either alone, formed into a pellet, in conjunction with one or more excipients, formed as part of a polymeric based release system such as co-extruded polymers or matrix polymer systems, or included as part of a delivery system based on mass transfer through an opening or a gel matrix, either by diffusion or osmotic pressure pumping of the active ingredient.

Typically one of the pellets 15, which is the rear pellet in the illustrated embodiment includes an antibiotic agent. A wide range of active ingredients may be employed as the antibiotic agent, such as macrolide antibiotics, especially tylosin and its salts, penicillin and derivatives thereof, tetracycline and its derivatives including oxytetracycline and their salts. As used herein the term antibiotic agent is intended to include antibiotics as noted above and other compositions that operably function under the present invention like antibiotics in preventing the formation of abscesses at the site of the puncture 21 as well as infection and inflammation. Such antibiotic agents include bacteriostats such as alcohols and glycols, anti-inflammatory agents, and any other suitable antibacterial, bacteriostat, anti-inflammatory or combination thereof. In certain embodiments anti-inflammatory ingredients are employed in order to control site inflammation, especially where drug delivery devices such as osmotic pumps are implanted.

Any of a number of excipients may be employed in the pellets 14, including polyethylene glycol, as sold under the trademark Carbowax®, by Union Carbide, magnesium stearate, cellulose and its derivatives, especially ethylcellulose as sold under the trademark Ethocel® by Dow, lactose, polymeric supports and binders and coloring agents.

In addition to antibiotic agents such as are found in pellet 15, the remaining pellets 14 are formulated to include pharmaceuticals such as insulin, endocrine hormones (such as growth and birth control hormones), vaccines, parasiticides or other biocides. Thus, in the illustrated embodiment one pellet 15 is an antibiotic agent and the remaining seven pellets 14 are non antibiotic agent pharmaceuticals, preferably one or more hormones. It is foreseen that the number of pellets for each group may vary or that the antibiotic agent and other non antibiotic pharmaceutical may be mixed in one or more of the pellets 14.

The pellets 14 are formulated so as to be biodegradable in the target animal 18 and to control release of the active ingredients. Preferred pellets 14 include excipients such as polyethylene glycol and tablet lubricants such as magnesium stearate and croscarmellose sodium, especially as sold under the trademark Ac-Di-Sol® by FMC. Pellets 14 may include a wide range of additives to facilitate application, to control release, to stabilize the composition and for other reasons well known in the art.

Each magazine chamber 30 is prefilled with a preferred number of discrete pellets 14, each containing a dose of one or more pharmaceuticals such as bovine growth hormone, along with at least one pellet 15 containing an antibiotic agent dose. The magazine strip 16 is preferably loaded onto implanter housing 22 in an orientation so that the pharmaceutical pellets 14 will be delivered first, followed by the antibiotic pellet 15.

Figure 2:
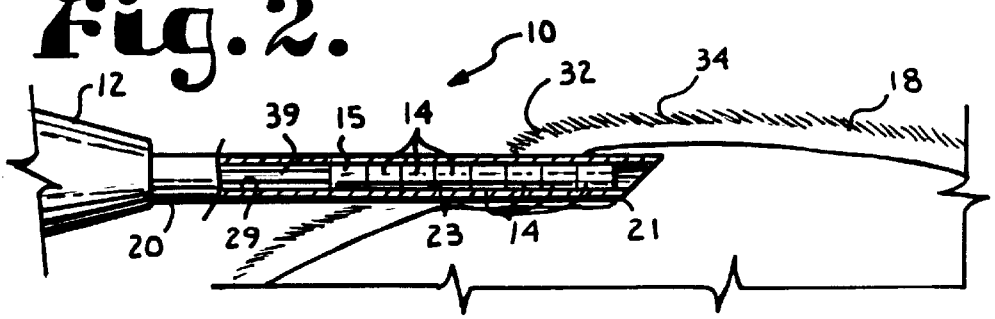
FIG. 2 is an enlarged, fragmentary cross-sectional view, taken along line 2—2 of FIG. 1, illustrating the hypodermic needle with pellets inside the needle being inserted into an ear of the cow.
Figure 3:
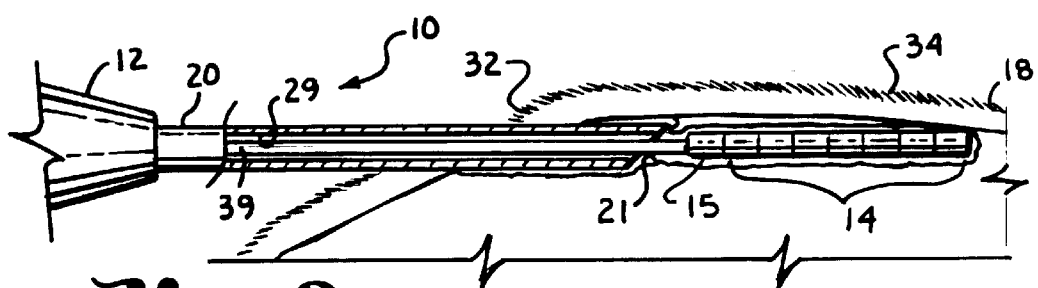
FIG. 3 is an enlarged, fragmentary cross sectional view similar to FIG. 2, illustrating subcutaneous placement of a stack of pellets by the implanter into the ear of the cow.

In use, an operator grasps the implanter 12 by the grip 24 and urges the needle 20 into the hide 32 and under the skin of the target animal 18 to make the implant receiving puncture 21. The puncture 21 shown in FIG. 2 is incomplete and the depth of the implant receiving puncture 21 shown in FIG. 2 is about half of the total depth as shown in FIG. 3. The operator 19 depresses the trigger member 26, thereby propelling a pin 39 of the impeller member 28 forwardly through an aligned magazine chamber 30, forcing the pellets 14 and 15 through the needle bore 36 and into the implant receiving puncture 21. The last pellet 15 contains the antibiotic agent dose. The operator 19 then withdraws the needle 20, leaving the pellets 14 and 15 in the implant receiving puncture 21.

While the pharmaceuticals in the pellets 14 are absorbed and utilized systemically by the animal 18, the antibiotic agent pellet 15 preferably delivers most of its dose at the site of the implant receiving puncture 21, although some of the antibiotic agent may be absorbed and carried systemically. The antibiotic pellet 15 is preferably specifically formulated to deliver its dose locally rather than systemically, and slowly, at a controlled, predetermined rate over a preselected period of time. This serves as a biocide against bacteria and other antibiotic treatable microbes which may have been introduced through the contaminated needle 20, which may have been resident on the animal hide 32 and drawn into the implant receiving puncture 21 by the needle 20, or which enters after the needle 20 is withdrawn. In this manner the antibiotic agent prevents or substantially reduces the likelihood of infection at the implant receiving puncture 21 after the needle 20 is withdrawn. It also serves to continue localized sustained delivery of an antibiotic agent until the implant receiving puncture 21 is fully healed about the pellets 14 and 15.

Those skilled in the art will appreciate that the magazine strip 16 may be loaded for selective injection of more than one antibiotic pellet 15. Where a number of pellets 14 of pharmaceutical are to be delivered, the pharmaceutical may be sandwiched between two or more antibiotic pellets to provide localized antibiotic release at both ends of a long implant receiving puncture 21. It is foreseen that in other embodiments antibiotic pellets may be alternated in a stack of pellets of other pharmaceuticals, for delivery throughout the implant receiving puncture 21.

The antibiotic pellet system 1 of the present invention may be employed efficaciously with cows, horses, sheep, swine, dogs, cats or any other suitable animal, including humans.

The following example is provided for the purpose of illustrating the invention and is not intended to be limiting upon the scope of the claims.

EXAMPLE 1

Two types of pellets, including antibiotic agent pellets, are formulated so as to have different characteristics with respect to release of active ingredients. The first type is quick release and the second type is controlled, sustained release, depending on the nature of the infection to be controlled.

The following formulation provides relatively quick release of active ingredient to the site of the implant receiving puncture:

Formula I

90% by weight tylosin tartrate 8.0% by weight polyethylene glycol as sold under the trademark PEG 8000® by Union Carbide 1.5% by weight magnesium stearate 0.5% by weight croscarmellose sodium as sold under the trademark Ac-Di-Sol® by FMC The following formulation provides release of active ingredients to the site of the implant receiving puncture over a period of two to five days:

Formula II

90% by weight oxytetracycline 8.0% by weight polyethylene glycol as sold under the trademark PEG 8000® by Union Carbide 2.0% by weight magnesium stearate

EXAMPLE 2

Pellets containing the antibiotic active ingredient tylosin tartrate were produced according to the following formulation:

Formula III 26 milligrams tylosin tartrate 12.5 milligrams polyethylene glycol as sold under the trademarks PEG 8000® and Carbowax® by Union Carbide 0.5 milligrams magnesium stearate The pellets were produced by compression on a rotary tablet press.

Twenty one cattle were implanted with pellets including progesterone and estradiol benzoate pharmaceutical implants as sold under the trademark IMPLUS C® by Ivy Laboratories, Inc. Sixteen out of the larger group of twenty one cattle were implanted with one pellet of the antibiotic agent of Formula III prepared according to the method of this example. The remaining five cattle received the pharmaceutical implant pellets only and were not implanted with an antibiotic agent. The five cattle that received no antibiotic agent served as controls. A dose of *Actinomyces pyogenes* was then administered to the exterior of the implant site of each of the twenty one cattle in order to try to initiate infection in the implant receiving puncture.

After ten days, the implant sites were checked for abscess formation. The control cattle exhibited an 80% rate of abscess formation, whereas the cattle implanted with the antibiotic pellet of Formula III exhibited only a 33% incidence of abscess formation.

EXAMPLE 3

Pellets containing the active antibiotic agent tylosin tartrate were produced according to the following formulation:

Formula IV 35 milligrams tylosin tartrate 3 milligrams polyethylene glycol as sold under the trademarks PEG 8000® and Carbowax® by Union Carbide 0.4 milligrams magnesium stearate The pellets were produced by compression on a rotary tablet press.

Thirty six cattle were implanted with the same pharmaceutical identified in Example 2 and including progesterone and estradiol benzoate. Twenty-one of the larger group of thirty six cattle were simultaneously also implanted with a single pellet prepared according to Formula IV. The remaining fifteen cattle that did not receive antibiotic agent pellets served as controls. A dose of *Actinomyces pyogenes* was then administered to the exterior of the implant site of each of the thirty six cattle in order to try to initiate infection in the puncture.

After eight days, the implant sites were checked for abscess formation. The control cattle exhibited a 93% rate of abscess formation, whereas the cattle implanted with the antibiotic agent pellet exhibited only a 25% incidence of abscess formation.

It is to be understood that while certain forms of the present invention have been illustrated and described herein, it is not to be limited to the specific forms or arrangement of parts described and shown.

What is claimed and desired to be secured by Letters Patent is as follows:

1. A method of reducing the likelihood of the development of an infection in an animal at the site of a subdermal placement of a pharmaceutical pellet; said method comprising the steps of:
    (a) providing an implanter apparatus for implanting pharmaceutical pellets in an animal through the bore of a hypodermic needle which is operably coupled to a pellet magazine;
    (b) loading the pellet magazine with a non antibiotic pharmaceutical pellet dose in a first pellet and an antibiotic agent pellet dose in a second pellet; said first and second pellets being separate and discrete;
    (c) inserting the hypodermic needle under the skin of the animal and injecting the pharmaceutical dose and the antibiotic agent dose in a single injection; and
    (d) withdrawing the hypodermic needle from under the skin of the animal so as to leave the pharmaceutical pellet dose and antibiotic agent dose beneath the skin.

2. The method according to claim 1 including the step of selecting the antibiotic agent pellet dose from the group consisting of antibiotics, bacteriostats and anti-inflammatory compositions.

3. The method according to claim 1 including the step of providing a plurality of discrete pellet doses.

4. The method according to claim 1 including the steps of:
    (a) inserting the hypodermic needle under the skin of the animal and injecting a pharmaceutical pellet dose; and while
    (b) maintaining the hypodermic needle in place under the skin of the animal, sequentially injecting an antibiotic agent pellet dose.

5. The method according to claim 4 including the steps of:
    (a) first injecting the pharmaceutical pellet dose; and
    (b) thereafter while maintaining the hypodermic needle in place under the skin of the animal, injecting the antibiotic agent pellet dose such that the antibiotic agent dose is closest to the skin of the animal.

6. In a method of administering a subcutaneous implant to an animal, the improvement comprising:
    (a) injecting an implant for retention under the skin of the animal including a first pharmaceutical dose and a second antibiotic dose in a single injection.

7. The method according to claim 6 including:
    (a) selecting said antibiotic dose to provide an antibiotic that operably functions to reduce the likelihood of infection about said pellets and that is compatible with the animal.

8. A method of providing localized sustained antibiotic release at an injection site comprising:
    (a) providing an implanter apparatus for implanting pharmaceutical pellets in an animal through the bore of a hypodermic needle which is operably coupled to a pellet magazine;
    (b) loading the pellet magazine with a plurality of pellets including at least one non antibiotic pharmaceutical pellet and at least one antibiotic pellet; said pharmaceutical pellet and said antibiotic pellet being separate and discrete;
    (c) inserting the hypodermic needle under the skin of an animal and selectively injecting the pharmaceutical pellet;

(d) maintaining the hypodermic needle in place under the skin of the animal and also selectively injecting the antibiotic pellet;

(e) withdrawing the hypodermic needle from under the skin of the animal while leaving said pellets beneath the skin of the animal.

9. The method according to claim 8 including positioning said antibiotic pellet such that it is the closest of the pellets to the skin.

10. The method according to claim 8 including a slow release antibiotic.

11. An implant for subcutaneous implantation in an animal comprising:

(a) at least one antibiotic agent pellet; and (b) at least one non-antibiotic pharmaceutical pellet; said antibiotic agent pellet and said pharmaceutical pellet being separate and discrete; all of said pellets being joined side by side in a single unit for implantation into the same site.

12. The implant according to claim 11 including:

(a) an excipient, where said antibiotic agent pellet comprises a composition selected from the group consisting of antibiotics, bacteriostats and anti-inflammatories.

13. The implant according to claim 11 wherein:

(a) said antibiotic agent pellet comprises a local acting antibiotic.

14. The implant according to claim 12 further including:

(a) a lubricant located on the exterior of said implant.

* * * * *